(12) United States Patent
Sessions et al.

(10) Patent No.: US 6,349,828 B1
(45) Date of Patent: *Feb. 26, 2002

(54) TAMPER EVIDENT PACKAGING

(75) Inventors: Robert W. Sessions, Hinsdale; Rainer Schmeichel, Glen Ellyn, both of IL (US)

(73) Assignee: Ferris Pharmaceuticals Inc., Burr Ridge, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 412 days.

(21) Appl. No.: 08/797,478

(22) Filed: Feb. 6, 1997

(51) Int. Cl.$^7$ .............................................. B61B 17/06
(52) U.S. Cl. ...................................... 206/440; 206/807
(58) Field of Search ............................... 206/439, 440, 206/807, 824, 484; 383/5, 210, 211; 229/87.05

(56) References Cited

U.S. PATENT DOCUMENTS

| | | | | |
|---|---|---|---|---|
| 3,001,689 A | * | 9/1961 | Burton | 229/62 |
| 3,510,054 A | * | 5/1970 | Sanni et al. | 229/66 |
| 3,642,126 A | * | 2/1972 | Kurtz et al. | 206/63.3 |
| 3,899,080 A | * | 8/1975 | Brunda | 206/531 |
| 3,938,659 A | * | 2/1976 | Wardwell | 206/440 |
| 4,119,128 A | * | 10/1978 | Bishop | 206/807 |
| 4,537,312 A | * | 8/1985 | Intini | 206/531 |
| 4,566,627 A | * | 1/1986 | Gendron | 206/807 |
| 4,884,563 A | | 12/1989 | Sessions | |
| 5,064,653 A | | 11/1991 | Sessions et al. | |
| 5,065,752 A | | 11/1991 | Sessions et al. | |
| 5,164,178 A | * | 11/1992 | Muysson | 424/76.4 |
| 5,181,610 A | * | 1/1993 | Quick et al. | 383/210 |
| 5,252,301 A | | 10/1993 | Sessions et al. | |
| 5,346,301 A | * | 9/1994 | Scarberry et al. | 383/5 |
| 5,352,041 A | * | 10/1994 | Fullerton et al. | 383/5 |
| 5,372,428 A | * | 12/1994 | Bruno et al. | 383/5 |
| 5,472,093 A | * | 12/1995 | Nugent et al. | 206/532 |
| 5,511,665 A | * | 4/1996 | Dressel et al. | 206/532 |

FOREIGN PATENT DOCUMENTS

DE 3342-256 * 6/1985 ................. 383/5

* cited by examiner

*Primary Examiner*—Shian Luong
(74) *Attorney, Agent, or Firm*—Leydig, Voit & Mayer, Ltd.

(57) ABSTRACT

Tamper-evident packaging for a product, e.g., a wound dressing or other sterile medical device. The packaging comprises a top sheet and a bottom sheet, the top sheet sealed to the bottom sheet about the product so as to seal the product between the top and bottom sheets, wherein the portion of the top and bottom sheets that are sealed to each other define sealing areas. The top sheet has at least one perforation in its sealing area so that when the sheets are separated from one another, the top sheet tears adjacent to the at least one perforation, indicating that the package has been at least partially opened.

12 Claims, 4 Drawing Sheets

TAMPER EVIDENT PACKAGING

BACKGROUND OF THE INVENTION

1. Field of the Invention

The present invention relates to tamper-evident packaging for a product, such as, e.g., wound dressings.

2. Background

Tamper-evident packaging has been used for many years on a wide variety of consumable products. Examples of products that employ such packaging include food, drugs, and items that must be maintained in a sterile condition prior to use, such as medical products.

Wound dressings are exemplary of one such medical product that must be maintained in a sterile condition prior to use. One long-standing problem associated with packaged wound dressings, however, is assuring that a dressing which is to be applied onto a wound is in fact sterile prior to use. When wound dressings leave their point of manufacture, they are sterile and are packaged in a manner that ensures their sterility until use. However, at the hospital or other health care facility, a dressing is sometimes removed from its packaging, and pieces cut therefrom to fit the size of the wound. Any remaining unused dressing, with its sterility now compromised, is sometimes returned to the packaging and an effort made to reseal the packaging in order to allow the unused (and now non-sterile) portion of the dressing to be used at some future date. This practice, undertaken as a cost-saving measure, is contrary to the manufacturer's instructions and has the potential to introduce bacteria and other microorganisms into the wound situs, compromising the health of the patient.

Thus, a need exists for a means to enable a user to readily determine whether the packaging of a wound dressing has been previously opened, and the sterility of the wound dressing packaged therein compromised.

SUMMARY OF THE INVENTION

An object of the present invention is to provide a packaging system which includes a tamper-evident feature so that a user of the packaged product can readily determine whether the package has previously been opened. This packaging system is advantageously used in connection with products that are required to be sterile prior to use, such as wound dressings and other medical products. Additional inventive features will be apparent from the description of the invention provided herein.

In accordance with the foregoing, one embodiment of the present invention provides tamper-evident packaging for a product comprising a top sheet and a bottom sheet. The top sheet is sealed to the bottom sheet about the product so as to seal the product between the top and bottom sheets. The portion of the top and bottom sheets that are sealed to each other define a sealing area with respect to each sheet. The top sheet includes at least one perforation in its sealing area so that when the sheets are separated from one another, the top sheet tears adjacent to the at least one perforation, thereby indicating that the package has been at least partially opened.

The foregoing and other features and advantages of the present invention will be more readily apparent upon reading the following description of a preferred exemplified embodiment of the invention and upon reference to the accompanying drawings wherein:

While the invention will be described and disclosed in connection with certain preferred embodiments and procedures, it is not intended to limit the invention to those specific embodiments. Rather it is intended to cover all such alternative embodiments and modifications as fall within the spirit and scope of the invention.

DESCRIPTION OF THE PREFERRED EMBODIMENTS

In accordance with the teachings of the present invention, a tamper-evident packaging system is provided which addresses, among others, the problems associated with the use of previously opened wound dressings, or other products that should be sterile prior to use, in the treatment of patients. While the packaging of the present invention finds particular application in connection with wound dressings, it may also be used in connection with other medical products which are required to be sterile prior to use, or indeed with any other product where the use of tamper-evident packaging is desired. However, and for purposes of convenience only, the discussion herein will be limited to the use of this packaging in connection with a relatively thin wound dressing product, such as, e.g., POLYMEM® dressings sold by Ferris Manufacturing Corporation, Burr Ridge, Ill., and those described in U.S. Pat. Nos. 5,064,653, 5,065,752 and 5,254,301.

Figure 1:
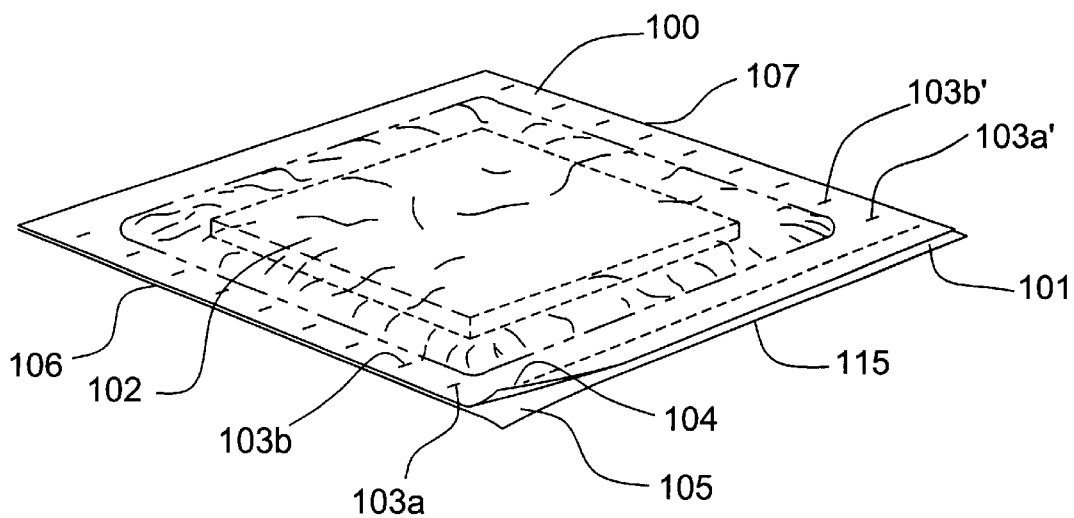
FIG. 1 is a perspective view of one embodiment of the tamper-evident packaging constructed in accordance with an aspect of the present invention, wherein the packaged product is a wound dressing.

One embodiment of the tamper-evident packaging of the present invention is illustrated in FIG. 1. In this embodiment, the tamper-evident packaging is shown as comprising a top sheet 100 and a bottom sheet 101, with a wound dressing 102 being shown as the product being packaged. The top sheet 100 has also been provided with one or more perforations (e.g., notches, holes or slits) 103*a*, 103b,103a', 103b'; which perforations may, if desired, extend through the bottom sheet 101. These perforations, in conjunction with the top sheet and sealing means utilized in the packaging, function together to provide the tamper-evident features of the present invention. These features will be described in more detail in the following paragraphs.

The top 100 and bottom 101 sheets used in the present packaging may comprise any suitable material so long as the tamper-evident features of the packaging are not compromised. Similarly, the top 100 and bottom 101 sheets need not comprise the same material. Examples of suitable materials for the top 100 and bottom 101 sheets include medical grade bleached Kraft papers, plastics, foils or combinations thereof. In general, a suitable material should be able to be torn after being adhered to itself (or to a second material of different composition) in accordance with the present invention.

Advantageously, and in connection with providing tamper-evident packaging for a medical product, e.g., a wound dressing, the sheet material should also be able to undergo a sterilization process without degrading and be able to retain the product therein in a sterile condition thereafter. Preferably, the material should be able to accept a permanent ink during printing and, for production efficiencies, be available in web form.

Rexam Medical Packaging LWC-027 is an example of a preferred sheet material because it is compatible with a variety of sterilization processes, impermeable to microorganisms, available in web form, and has sufficient strength and shelf life to retain (with routine handling) the product in a sterile condition prior to use.

As exemplified in FIG. 1, one (or both) of the sheets may, if desired, extend beyond their respective sealing areas so as to provide indicating tabs 104, 105. Such tabs, which are not sealed to one another, will allow a user to readily grasp each sheet individually, thus facilitating rapid opening of the packaging.

Figure 2:
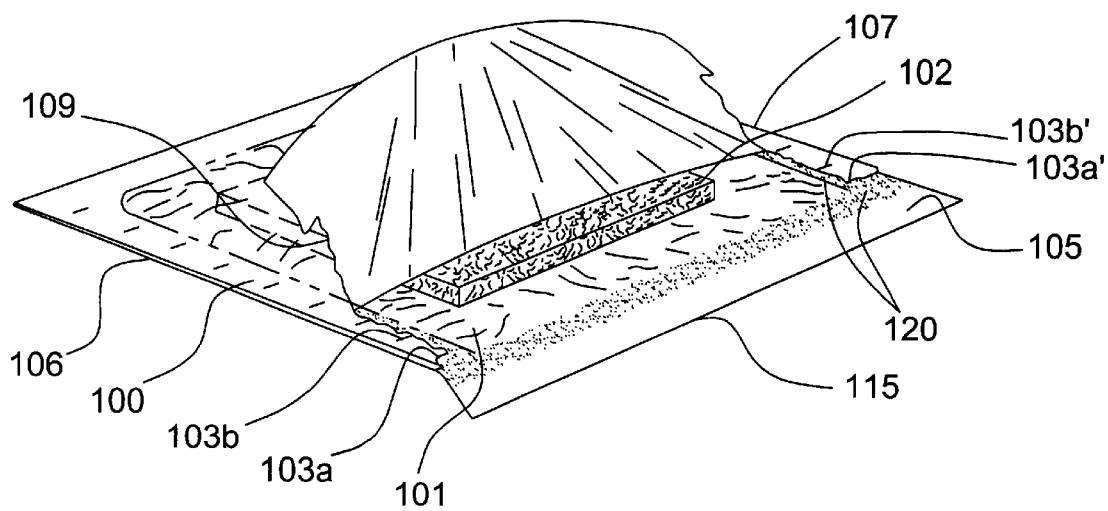
FIG. 2 is a perspective view of the embodiment of the tamper-evident packaging set forth in FIG. 1 which provides an example of the tearing of the top sheet which occurs when the top and bottom package sheets are separated at a perforation.
Figure 7:
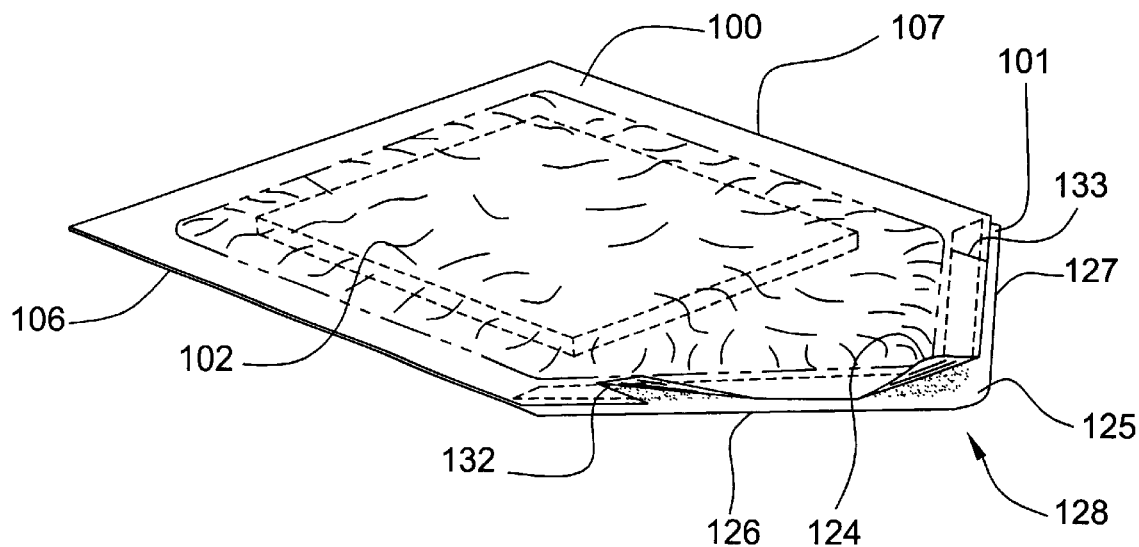
FIG. 7 is a perspective view of a fourth embodiment of the tamper evident packaging constructed in accordance with an aspect of the present invention.
Figure 8:
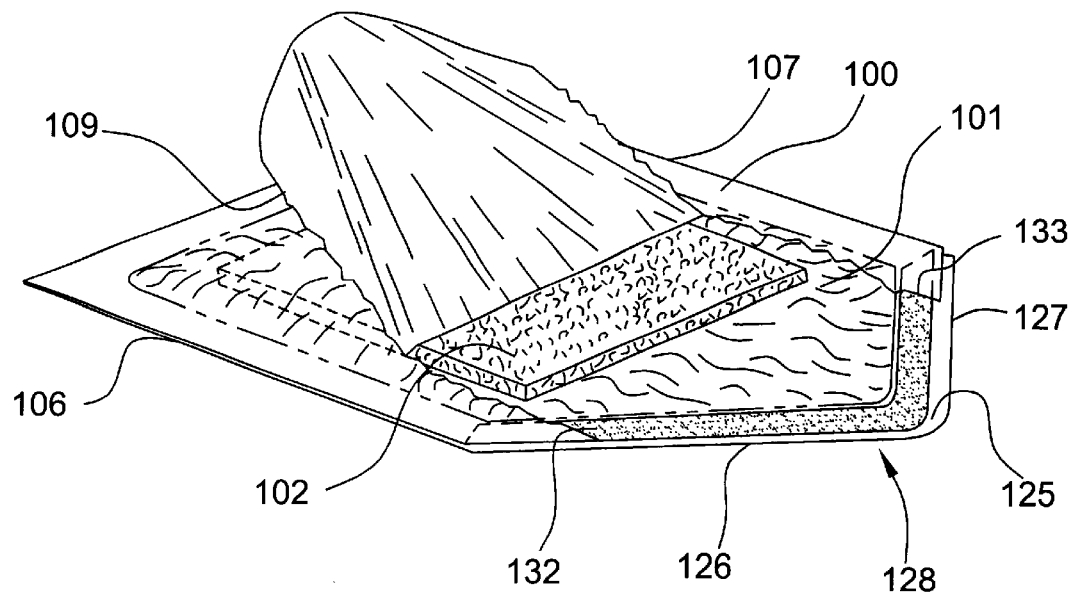
FIG. 8 is a perspective view of the embodiment of the tamper evident packaging set forth in FIG. 7 which provides an example of the tearing of the top sheet which occurs when the top and bottom package sheets are separated at a perforation.

Any continuous or non-continuous process suitable for providing a packaged product can be adapted and used to provide the tamper-evident packaging of the present invention, so long as the features as described herein are not compromised. For example, the top and bottom sheets may be pre-cut to the appropriate size of the product to be packaged or, if a continuous method of packaging is utilized, the sheets may be cut to size from a continuous web. While the sheets may be of any suitable shape, they are generally contemplated to be either square or rectangular, depending upon the shape of the product, with any indicating tabs being located on or along one side of such packaging, as shown in FIGS. 1–2. However, other shapes may be used, for example, FIGS. 7–8 illustrate an embodiment of the present invention wherein the packaging is chevron-shaped and the indicating tabs 124, 125 are located on the two edges 126, 127 which form the front end 128 of the packaging.

As indicated previously, the top sheet 100 is sealed to the bottom sheet 101 about the product so as to seal the product between the top and bottom sheets. Each sheet has a sealing area, which is defined by that portion of the sheet that is sealed to the other sheet. The sealing area of each sheet may extend maximally within the area bounded by the outer periphery of the product sealed in the packaging and the outer periphery, or edge, of each sheet. By way of example, the sealing area of each sheet may extend from a few millimeters from the outer periphery of a wound dressing to the outer periphery or edges of each sheet with the exception, of course, of any portion of each sheet that may form an indicating tab. See, e.g., FIGS. 1–6.

The sealing of the top and bottom sheets to one another may be accomplished by any suitable means, so long as the tamper-evident features of the present invention are realized in the finished package. By way of example, the sealing means 120 selected should, at a minimum, provide sufficient "adhesion" between the top and bottom sheets so that when the sheets are separated from one another, at least one perforated sheet tears adjacent to one of its perforations. See, e.g., the embodiments set forth in FIGS. 2, 4, 6 and 8 which demonstrate examples of such tearing of the top sheet 100 wherein the tear 109 in the top sheet extends from the perforation itself. It is contemplated that such tearing will alert any potential user of the packaged product that the seal of the packaging has been broken. When the packaged product is a sterile wound dressing, the tearing indicates that the sterility of the wound dressing has been compromised, and that it should not be used. This simple yet effective signal allows a user to readily identify any package that has been subjected to tampering, even if care has been taken in an attempt to re-seal the package.

Sealing the top and bottom sheets may advantageously be accomplished by any of a number of methodologies, e.g., heat seal, ultrasonic, RF seal, or adhesives, all of which are well-known to those of ordinary skill. Examples of suitable adhesives include heat or cold sealable adhesives. Particularly preferred are pressure sensitive adhesives, with latex-free adhesives being most preferred.

In providing the aforesaid seal using an adhesive, one or both sheets may be coated with the adhesive in their entirety, or the adhesive may be applied to only a portion of the sheets, depending upon the requirements of the user. One method of applying the adhesive comprises simply flood-coating the interior surface of the bottom sheet 101 (and/or the top sheet 100, if desired) with the adhesive. Of course, when such flood coating is utilized, the product being packaged, e.g., wound dressing, and the adhesive should be selected so that the product does not unduly adhere to the sheet, e.g., such that the product is damaged upon removal from the packaging. Packaging sheets suitable for use in connection with the present invention having a hot or cold seal type of adhesive coated thereon are available from DRG Medical Packaging, Madison, Wis.

Those of ordinary skill will have no difficulty, based upon the description provided herein, in selecting the appropriate sheet material and method of sealing the sheets to one another that will provide the tamper-evident features associated with the present invention.

In accordance with the present invention, and with respect to the location of the perforations used therein, at least a portion of one such perforation should be located within the sealing area of a sheet. However, and as those skilled in the art will appreciate after reviewing the description provided herein, the perforations may be provided in varying shapes and patterns without compromising the tamper-evident features of the present invention. For example, in the embodiment of the tamper-evident packaging shown in FIGS. 1 and 2, the perforations 103 are in the form of slits that are located wholly within the sealing area and adjacent to the two edges 106, 107 of the packaging, and are further generally parallel to the direction of opening (i.e., perpendicular to the front edge 115 which includes the indicating tabs 104, 105). Those perforations may also be present in both the top 100 and bottom 101 sheets (not shown), in either an offset or matching pattern. In the latter case, the perforations would be advantageously introduced into the packaging after the top 100 and bottom 101 sheets were sealed, the perforations extending through both the top and bottom sheets of the package.

Figure 3:
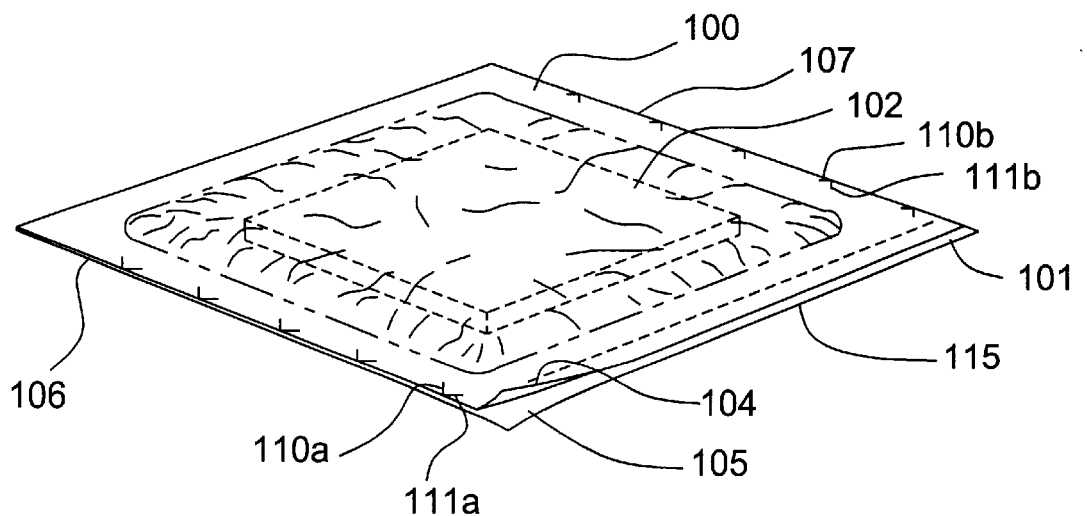
FIG. 3 is a perspective view of a second embodiment of the tamper-evident packaging constructed in accordance with an aspect of the present invention, wherein the packaged product is a wound dressing.
Figure 4:
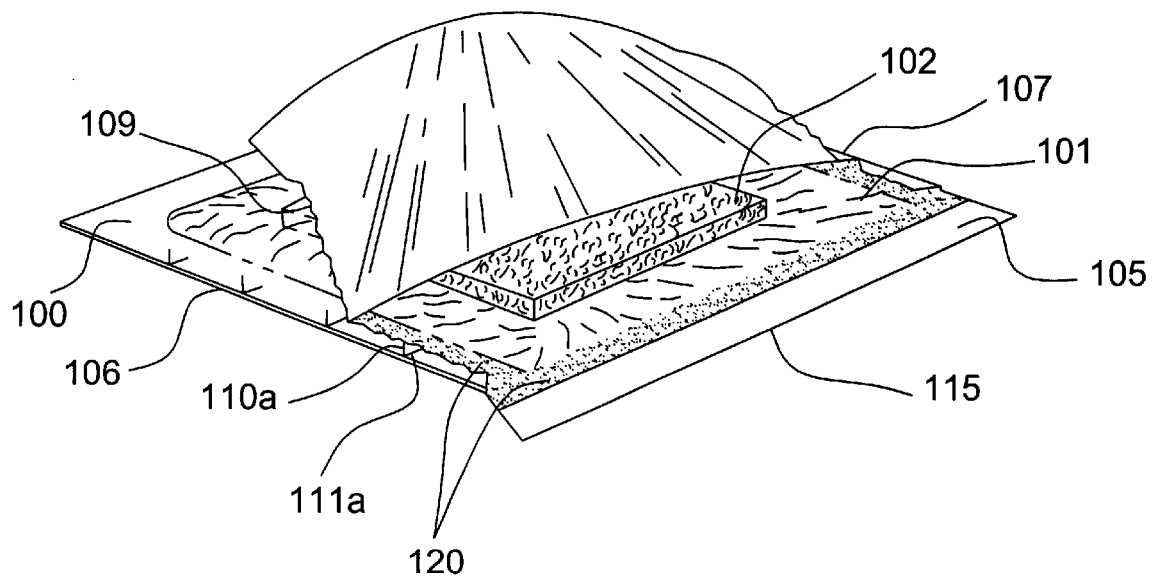
FIG. 4 is a perspective view of the embodiment of the tamper evident packaging shown in FIG. 3, which provides an example of the tearing of the top sheet which occurs when the top and bottom package sheets are separated at a perforation.
Figure 5:
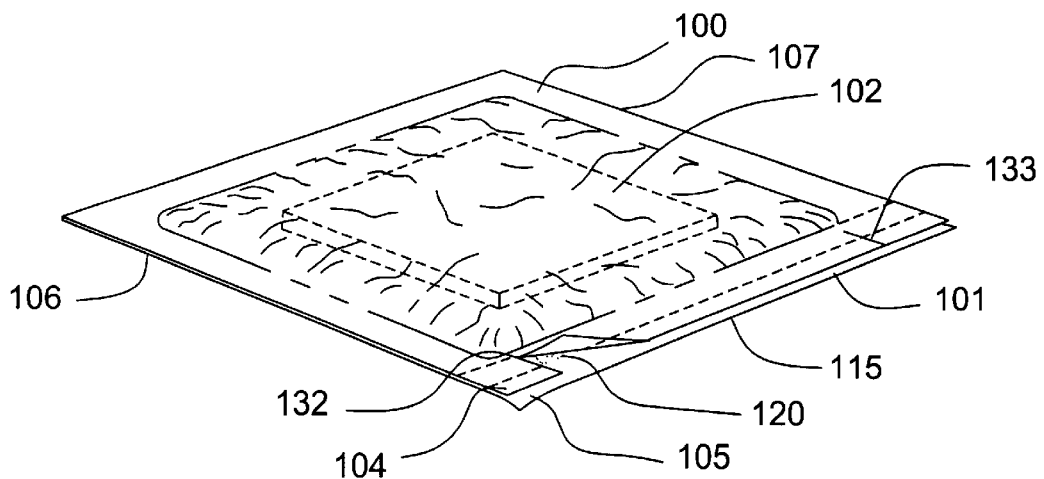
FIG. 5 is a perspective view of a third embodiment of the tamper evident packaging constructed in accordance with an aspect of the present invention.

By way of further example, and advantageously, the slits range in length from about 1 mm to about 5 mm or more, and are preferably oriented in the manner set forth in FIG. 1, i.e., perpendicular to the direction of opening. Another type of perforation pattern is shown in FIGS. 3 and 4, wherein two notches 110a, 111a and 110b, 111b, are cut through the sheets adjacent the edges 106, 107 of the packaging. This pattern is preferred because of cost efficiency and manufacturing ease. In such a case, the bottom sheet 101, as well as the top sheet 100, may sustain tearing as the packaging is opened.

Figure 6:
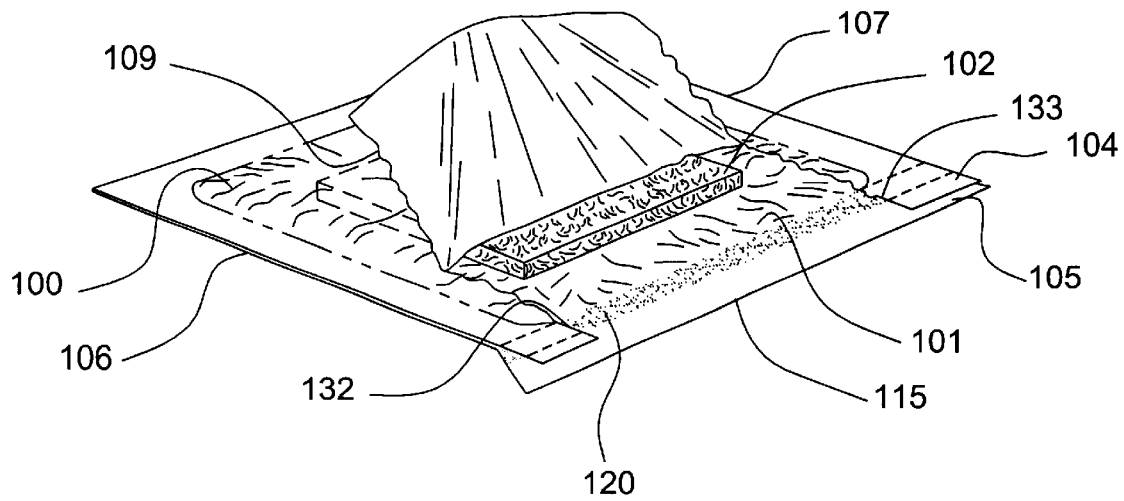
FIG. 6 is a perspective view of the embodiment of the tamper evident packaging set forth in FIG. 5, which provides an example of the tearing of the top sheet which occurs when the top and bottom package sheets are separated at a perforation.

FIGS. 5–8 illustrate yet another configuration for the perforations. In particular, the embodiments of the invention shown in FIGS. 5–8 disclose two slits 132, 133 cut in the indicating tab 104 (FIGS. 5–6), 124 (FIGS. 7–8) that extend into the sealing area of the sheets at the front end of the packaging. One of the slits 132, 133 is located near each of the side edges 106, 107 and the slits 132, 133 are oriented generally parallel to the direction of opening (as shown in FIGS. 6 and 8).

The foregoing is not intended to limit the types of wound dressings, or sizes thereof, that may be employed in connection with the tamper-evident packaging of the present invention. It is further intended that invention include all modifications encompassed within the spirit and the scope of the invention as defined by the following claims.

What is claimed is:

1. A tamper-evident sealed package for a product comprising a top sheet and a bottom sheet, the top sheet sealed to the bottom sheet so as to seal the product between the top and bottom sheets and provide a sealed package, the portion of the top and bottom sheets that are sealed to each other defining sealing areas, wherein at least a portion of the top sheet and a portion of the bottom sheet include tabs which extend beyond the sealing area and are not sealed to one another, the top sheet of the sealed package having at least one perforation in its sealing area so that when the sheets are separated from one another by relative movement of the tabs, the top sheet tears adjacent to the at least one perforation to provide an indication that the sealed package has been at least partially opened.

2. The tamper-evident packaging according to claim 1, wherein the top and bottom sheets, when sealed to each other, provide the packaging with at least two substantially parallel edges, wherein the sealing areas extend to the substantially parallel edges, and wherein the top sheet contains perforations adjacent to each of those edges.

3. The tamper evident packaging according to claim 2, wherein the top and bottom sheets include perforations.

4. The tamper-evident packaging according to claim 3, wherein the perforations extend through the top and bottom sheets.

5. The tamper-evident packaging according to claim 2, wherein at least some of the perforations extend inwardly from the edges of the packaging.

6. The tamper-evident packaging according to claim 1 wherein the packaging has at least one edge which includes indicating tabs and the at least one perforation extends inwardly from the indicating tab.

7. The tamper-evident packaging according to claim 1, wherein the top and bottom sheets are chevron-shaped.

8. A tamper-evident sealed package for a product comprising a top sheet and a bottom sheet, the top sheet sealed to the bottom sheet so as to seal the product between the top and bottom sheets and provide a sealed package with at least two opposing edges, the portion of the top and bottom sheets that are sealed to each other defining sealing areas, wherein at least a portion of the top sheet and a portion of the bottom sheet include tabs which extend beyond the sealing area and are not sealed to one another, the sealing areas including the portions of the top and bottom sheets adjacent the opposing edges, the top sheet of the sealed package having at least one perforation in its sealing area adjacent each of the opposing edges so that when the sheets are separated from one another by relative movement of the tabs, the top sheet tears adjacent to the at least one perforation to provide an indication that the sealed package has been at least partially opened.

9. The tamper-evident packaging according to claim 8 wherein the top sheet includes a plurality of perforations adjacent the opposing edges.

10. The tamper evident packaging according to claim 9, wherein the top and bottom sheets include perforations.

11. The tamper-evident packaging according to claim 10, wherein the perforations in the top sheet extend through the bottom sheet.

12. The tamper-evident packaging according to claim 9, wherein at least some of the perforations extend inwardly from the edges of the packaging.

* * * * *